United States Patent
Scioscia et al.

(10) Patent No.: US 9,642,652 B2
(45) Date of Patent: May 9, 2017

(54) VARIABLE ANGLE BONE PLATE WITH SEMI-CONSTRAINED ARTICULATING SCREW

(71) Applicant: Choice Spine, LP, Knoxville, TN (US)

(72) Inventors: Thomas N. Scioscia, Midlothian, VA (US); Raymond J. Cloutier, Alachua, FL (US); Jason A. McAtamney, Gainesville, FL (US)

(73) Assignee: Choice Spine, LP, Knoxville, TN (US)

( * ) Notice: Subject to any disclaimer, the term of this patent is extended or adjusted under 35 U.S.C. 154(b) by 0 days.

(21) Appl. No.: 14/179,027

(22) Filed: Feb. 12, 2014

(65) Prior Publication Data

US 2014/0236241 A1   Aug. 21, 2014

Related U.S. Application Data

(60) Provisional application No. 61/764,378, filed on Feb. 13, 2013.

(51) Int. Cl.
*A61B 17/80*   (2006.01)
*A61B 17/70*   (2006.01)

(52) U.S. Cl.
CPC ...... *A61B 17/7059* (2013.01); *A61B 17/8047* (2013.01)

(58) Field of Classification Search
CPC ............ A61B 17/8057; A61B 17/8047; A61B 17/8605; A61B 17/7059; A61B 17/8061; A61B 17/8042; A61B 17/8033; A61B 17/8038; A61B 17/808; A61B 17/1728; A61B 17/8014; A61B 17/80

USPC ...................................... 606/70–71, 280–299
See application file for complete search history.

(56) References Cited

U.S. PATENT DOCUMENTS

| | | | |
|---|---|---|---|
| 3,433,510 A | | 3/1969 | Hulterstrum |
| 5,344,421 A | * | 9/1994 | Crook ............................ 606/281 |
| 5,549,612 A | * | 8/1996 | Yapp et al. .................... 606/293 |
| 5,800,435 A | | 9/1998 | Errico et al. |
| 5,904,683 A | * | 5/1999 | Pohndorf et al. ............. 606/287 |
| 6,139,550 A | * | 10/2000 | Michelson ....................... 606/70 |
| 6,193,721 B1 | | 2/2001 | Michelson |
| 6,258,089 B1 | * | 7/2001 | Campbell et al. ........... 606/86 B |
| 6,361,537 B1 | * | 3/2002 | Anderson ................... 606/86 B |
| 6,398,783 B1 | | 6/2002 | Michelson |
| 6,527,776 B1 | | 3/2003 | Michelson |

(Continued)

*Primary Examiner* — Eduardo C Robert
*Assistant Examiner* — Michelle C Eckman
(74) *Attorney, Agent, or Firm* — Luedeka Neely Group, PC

(57) ABSTRACT

In some embodiments, a cervical plate may include an elongate plate which bridges, during use, substantially adjacent vertebrae by anchoring the plate to the vertebrae. The cervical plate may include a plurality of openings extending through the elongate plate. The cervical plate may include plurality of bone fasteners. The bone fasteners may include a head and a shaft. The shaft may be positionable, during use, in the opening such that the shaft engages, during use, at least one of the vertebrae such that the bone fasteners couple the elongate plate to the vertebrae. The cervical plate may include a securing mechanism. The securing mechanism may, when activated, inhibit removal of at least one of the bone fasteners and inhibit movement of at least the shaft of the bone fastener in a lateral direction, while allowing movement of at least the shaft of the bone fastener along a substantially sagittal plane.

30 Claims, 11 Drawing Sheets

(56) References Cited

U.S. PATENT DOCUMENTS

| | | | | |
|---|---|---|---|---|
| 6,602,255 | B1* | 8/2003 | Campbell et al. | 606/290 |
| 6,652,525 | B1* | 11/2003 | Assaker et al. | 606/296 |
| 7,025,769 | B1* | 4/2006 | Ferree | 606/281 |
| 7,041,105 | B2* | 5/2006 | Michelson | 606/70 |
| 7,662,154 | B2* | 2/2010 | Ribeiro | 606/69 |
| 7,674,279 | B2* | 3/2010 | Johnson | 606/295 |
| 7,704,255 | B2 | 4/2010 | Michelson | |
| 7,857,836 | B2* | 12/2010 | Huebner et al. | 606/280 |
| 7,909,852 | B2 | 3/2011 | Boomer et al. | |
| 8,057,521 | B2* | 11/2011 | Smisson et al. | 606/288 |
| 8,066,750 | B2* | 11/2011 | Oi et al. | 606/289 |
| 8,109,974 | B2 | 2/2012 | Boomer et al. | |
| 8,118,847 | B2* | 2/2012 | Wallenstein et al. | 606/286 |
| 8,167,919 | B2* | 5/2012 | Foley et al. | 606/290 |
| 8,172,842 | B2* | 5/2012 | Sasing | 606/71 |
| 8,262,711 | B2* | 9/2012 | Hess | 606/282 |
| 8,328,855 | B2* | 12/2012 | Worcel | 606/290 |
| 8,372,152 | B2* | 2/2013 | Kirschman | 623/17.16 |
| 8,403,970 | B1* | 3/2013 | Bedor | 606/289 |
| 8,409,259 | B1* | 4/2013 | Bedor | 606/289 |
| 8,574,270 | B2* | 11/2013 | Hess et al. | 606/282 |
| 8,591,556 | B2* | 11/2013 | Hansell et al. | 606/289 |
| 8,652,182 | B1* | 2/2014 | Walker et al. | 606/296 |
| 8,690,923 | B2 | 4/2014 | Lynch | |
| 8,702,766 | B2* | 4/2014 | Mueller | 606/295 |
| 8,728,129 | B2* | 5/2014 | Fritzinger et al. | 606/290 |
| 8,858,603 | B1* | 10/2014 | Zufelt | 606/289 |
| 8,882,814 | B2* | 11/2014 | Suh | 606/289 |
| 8,940,030 | B1* | 1/2015 | Stein et al. | 606/294 |
| 9,039,744 | B2* | 5/2015 | Goodman et al. | 606/289 |
| 2002/0077630 | A1* | 6/2002 | Lin | 606/286 |
| 2002/0120273 | A1 | 8/2002 | Needham et al. | 606/61 |
| 2003/0040749 | A1 | 2/2003 | Grabowski et al. | 606/71 |
| 2003/0060828 | A1 | 3/2003 | Michelson | 606/71 |
| 2003/0078583 | A1 | 4/2003 | Biedermann et al. | 606/69 |
| 2003/0187440 | A1* | 10/2003 | Richelsoph et al. | 606/61 |
| 2004/0087951 | A1 | 5/2004 | Khalili | 606/69 |
| 2004/0127899 | A1* | 7/2004 | Konieczynski et al. | 606/69 |
| 2004/0127900 | A1* | 7/2004 | Konieczynski et al. | 606/69 |
| 2004/0127904 | A1* | 7/2004 | Konieczynski et al. | 606/70 |
| 2004/0220566 | A1* | 11/2004 | Bray | 606/69 |
| 2004/0220571 | A1* | 11/2004 | Assaker et al. | 606/69 |
| 2005/0021032 | A1 | 1/2005 | Koo | 606/69 |
| 2005/0075633 | A1 | 4/2005 | Ross | 606/61 |
| 2005/0085812 | A1* | 4/2005 | Sherman et al. | 606/61 |
| 2005/0085814 | A1* | 4/2005 | Sherman et al. | 606/61 |
| 2005/0149027 | A1* | 7/2005 | Campbell et al. | 606/70 |
| 2005/0192577 | A1* | 9/2005 | Mosca et al. | 606/69 |
| 2005/0234455 | A1* | 10/2005 | Binder et al. | 606/69 |
| 2005/0261689 | A1* | 11/2005 | Lin | 606/69 |
| 2005/0261690 | A1* | 11/2005 | Binder | A61B 17/8033 606/295 |
| 2005/0283152 | A1* | 12/2005 | Lindemann et al. | 606/61 |
| 2005/0288669 | A1 | 12/2005 | Abdou | |
| 2006/0122602 | A1* | 6/2006 | Konieczynski | A61B 17/7059 606/281 |
| 2006/0122603 | A1* | 6/2006 | Kolb | 606/69 |
| 2006/0122605 | A1* | 6/2006 | Suh et al. | 606/69 |
| 2006/0155285 | A1* | 7/2006 | Anderson | 606/70 |
| 2006/0200146 | A1* | 9/2006 | Doubler et al. | 606/69 |
| 2006/0217725 | A1* | 9/2006 | Suh | 606/71 |
| 2006/0235399 | A1* | 10/2006 | Carls et al. | 606/69 |
| 2006/0235403 | A1* | 10/2006 | Blain | 606/69 |
| 2006/0247639 | A1* | 11/2006 | Anderson | 606/69 |
| 2007/0123879 | A1* | 5/2007 | Songer et al. | 606/69 |
| 2007/0123884 | A1* | 5/2007 | Abdou | 606/69 |
| 2008/0015578 | A1* | 1/2008 | Erickson et al. | 606/61 |
| 2008/0097443 | A1* | 4/2008 | Campbell | 606/69 |
| 2008/0208263 | A1* | 8/2008 | Butler et al. | 606/286 |
| 2008/0287999 | A1* | 11/2008 | Markworth | 606/280 |
| 2009/0012571 | A1* | 1/2009 | Perrow et al. | 606/280 |
| 2009/0062863 | A1* | 3/2009 | Peppers | 606/289 |
| 2009/0157121 | A1* | 6/2009 | Harris et al. | 606/280 |
| 2009/0187218 | A1* | 7/2009 | Schaffhausen | 606/286 |
| 2009/0192549 | A1* | 7/2009 | Sanders et al. | 606/280 |
| 2010/0016901 | A1* | 1/2010 | Robinson | 606/289 |
| 2010/0042159 | A1* | 2/2010 | Butler | 606/286 |
| 2010/0049256 | A1* | 2/2010 | Jeon et al. | 606/289 |
| 2010/0121383 | A1* | 5/2010 | Stanaford et al. | 606/280 |
| 2010/0234899 | A1* | 9/2010 | Johnson et al. | 606/289 |
| 2010/0292737 | A1* | 11/2010 | Suh | 606/286 |
| 2011/0029023 | A1* | 2/2011 | Tornier | 606/289 |
| 2011/0118742 | A1* | 5/2011 | Hulliger et al. | 606/70 |
| 2011/0152945 | A1* | 6/2011 | Matityahu | 606/290 |
| 2011/0184415 | A1* | 7/2011 | Anderson et al. | 606/70 |
| 2011/0190770 | A1* | 8/2011 | Suh | A61B 17/80 606/70 |
| 2011/0245874 | A1 | 10/2011 | Boomer et al. | |
| 2011/0282389 | A1* | 11/2011 | Janice et al. | 606/264 |
| 2011/0313468 | A1* | 12/2011 | Robinson | 606/290 |
| 2011/0319893 | A1* | 12/2011 | Stanaford et al. | 606/70 |
| 2012/0010666 | A1* | 1/2012 | Songer | 606/286 |
| 2012/0065690 | A1* | 3/2012 | Perrow et al. | 606/294 |
| 2012/0095513 | A1* | 4/2012 | Humphreys | 606/289 |
| 2012/0143193 | A1* | 6/2012 | Hulliger | 606/70 |
| 2012/0158068 | A1* | 6/2012 | Humphreys | 606/286 |
| 2012/0179207 | A1* | 7/2012 | Mekhail | A61B 17/7059 606/281 |
| 2012/0191141 | A1* | 7/2012 | Costabile | 606/295 |
| 2012/0232595 | A1* | 9/2012 | Holschlag | 606/280 |
| 2012/0310289 | A1* | 12/2012 | Bottlang et al. | 606/291 |
| 2013/0006309 | A1* | 1/2013 | Lorio et al. | 606/281 |
| 2013/0023936 | A1* | 1/2013 | Altarac et al. | 606/279 |
| 2013/0060291 | A1* | 3/2013 | Petersheim | 606/305 |
| 2013/0184767 | A1* | 7/2013 | Kaufman et al. | 606/290 |
| 2013/0190825 | A1* | 7/2013 | Perrow et al. | 606/281 |
| 2013/0325074 | A1* | 12/2013 | Ziolo | 606/290 |
| 2014/0094856 | A1* | 4/2014 | Sinha | 606/291 |
| 2014/0128924 | A1* | 5/2014 | Perrow et al. | 606/287 |
| 2014/0172022 | A1* | 6/2014 | Suh | 606/291 |
| 2014/0243908 | A1* | 8/2014 | Konieczynski et al. | 606/289 |
| 2014/0243909 | A1* | 8/2014 | Campbell et al. | 606/290 |
| 2014/0276829 | A1* | 9/2014 | Hershgold et al. | 606/71 |
| 2014/0277182 | A1* | 9/2014 | Justis et al. | 606/293 |
| 2015/0094774 | A1* | 4/2015 | Swann et al. | 606/291 |
| 2015/0112395 | A1* | 4/2015 | Day et al. | 606/290 |

* cited by examiner

VARIABLE ANGLE BONE PLATE WITH SEMI-CONSTRAINED ARTICULATING SCREW

PRIORITY CLAIM

This application claims priority to U.S. Provisional Patent Application No. 61/764,378 entitled "VARIABLE ANGLE BONE PLATE WITH SEMI-CONSTRAINED ARTICULATING SCREW" filed on Feb. 13, 2013, which is incorporated by reference herein.

BACKGROUND OF THE INVENTION

1. Field of the Invention

The present disclosure generally relates to human system reinforcement devices and methods. More particularly, the disclosure generally relates to plates (e.g., cervical) used to fuse and/or reinforce vertebrae including securing mechanisms configured to selectively restrict movement of fasteners used in combination with the plates.

2. Description of the Relevant Art

There exist systems and methods for fusion of the human cervical spine, and in particular plate systems for aligning and maintaining cervical vertebrae in a selected spatial relationship (e.g., during spinal fusion of those vertebrae).

Currently cervical plating systems are used for this purpose. Such systems are composed of one or more plates and fastening screws for aligning and holding vertebrae in a desired position relative to one another. The earliest devices consisted of stainless steel plates and screws and required that the screws pass entirely through the vertebrae and into the spinal canal in order to engage the posterior cortex of the vertebral bodies. This required the ability to observe or visualize this area, which can be problematic in, for example, the lower cervical spine where the vertebrae may be hidden by obstructions.

In order to form holes in the vertebrae for the insertion of screws, the vertebrae must be drilled and tapped. Each of these operations involved the passage of an instrument entirely through the associated vertebrae and into the spinal column. Thus, these instruments come into close proximity to the spinal cord and the dural sac which are in close proximity to the back surfaces of the vertebrae. Any procedure which introduces an object into the spinal canal presents serious risks which are of concern to the surgeon.

In current plating systems, problems exist with failure of the hardware (e.g., breakage of the screws and plates, and backing out of screws). These occurrences may require surgical procedures to replace the broken parts or the plates and screws entirely, and to repair any damage that may have been caused.

The use of the known plating systems may result in a loss of lordosis (i.e., the normal curve of the cervical spine when viewed from the side).

Historically there have been many ways to prevent screws from backing out during anterior cervical/lumbar plating. These mechanisms are vast including everything from screws locking directly into the plate to screw cover mechanisms that prevent back out. However, current technology does not allow for controlled settling of the spinal column (leading, for example, to an increased risk of non-fusion). A benefit of controlled settling is that it increases the chance a fusion occurs because bone healing requires a good balance between stability and loading. This is called shared loading. The fracture must be kept stable during the healing process but not totally off-loaded or else the fracture will not unite.

A plate system optimally needs to inhibit lateral relative displacement of coupled vertebrae while at the same time allowing vertical relative displacement of the vertebrae which causes compressive loading on the intervening grafts which in turn leads to boney fusion.

Therefore a plating system and/or method which inhibits fastener back out while allowing movement of fasteners in substantially parallel to or in the sagittal plane would be highly desirable.

SUMMARY

This disclosure describes systems and methods for, in some embodiments, a cervical plate may include an elongate plate which bridges, during use, substantially adjacent vertebrae by anchoring the plate to the vertebrae. The elongate plate may have a first surface and a second surface opposite the first surface. The first surface may be positioned, during use, adjacent to at least a portion of a surface of the vertebrae. The cervical plate may include a plurality of openings extending through the elongate plate. The cervical plate may include plurality of bone fasteners. The bone fasteners may include a head and a shaft. The shaft may be positionable, during use, in the opening such that the shaft engages, during use, at least one of the vertebrae and the head is inhibited from being conveyed through the opening such that the bone fasteners couple the elongate plate to the vertebrae. The cervical plate may include a securing mechanism. The securing mechanism may, when activated, inhibit removal of at least one of the bone fasteners and inhibit movement of at least the shaft of the bone fastener in a lateral direction, while allowing movement of at least the shaft of the bone fastener along a plane that is substantially parallel to the sagittal plane.

In some embodiments, the securing mechanism, when activated, inhibits backing out of at least one of the bone fasteners from at least one of the plurality of openings. The securing mechanism, when activated, may inhibit removal of at least two of the bone fasteners from at least one of the plurality of openings. The at least two bone fasteners may be positioned substantially laterally relative to one another. In some embodiments, the securing mechanism, when activated, inhibits removal of at least four of the bone fasteners from at least one of the plurality of openings.

In some embodiments, the securing mechanism engages, when activated, a first side of a proximal end (e.g., the head or just below the head along the proximal end of the shaft) of the bone fastener. In some embodiments, the securing mechanism engages, when activated, a first side of the head of the bone fastener. The securing mechanism may engage, when activated, a first side of the head of the bone fastener such that a second side, opposite of the first side, of the bone fastener engages an adjacent portion of the cervical plate forming the opening in which the bone fastener is positioned forming a friction fitting.

In some embodiments, the securing mechanism may include a cam.

In some embodiments, the securing mechanism engages, when activated, a positionable member which moves from a first unengaged position to a second position engaging a first side of the head of the bone fastener forming a friction fitting.

In some embodiments, the securing mechanism engages, when activated, a deformable portion of the cervical plate deforming the deformable portion. When the deformable portion deforms, the deformable portion moves from a first unengaged position to a second position. The second position may engage a first side of the head of the bone fastener forming a friction fitting. In some embodiments, the deformable portion may include a ring which expands upon activation of the securing mechanism. In some embodiments, the securing mechanism comprises a screw which is conveyed, when the securing mechanism is activated, into an opening adjacent the deformable portion such that the conveyance of the screw into the opening deforms the deformable portion.

In some embodiments, the securing mechanism engages, when activated, a deformable portion of the cervical plate deforming the deformable portion. The deformable portion deforms such that an engaging portion coupled to the deformable portion moves from a first unengaged position to a second position engaging a first side of the head of the bone fastener forming a friction fitting.

In some embodiments, the securing mechanism may include a screw. The screw may be conveyed, when the securing mechanism is activated, into an opening such that a head of the screw engages a first side of the head of the bone fastener. The screw may engage the first side of the bone fastener such that a second side, opposite of the first side, of the bone fastener engages an adjacent portion of the cervical plate forming the opening in which the bone fastener is positioned forming a friction fitting.

In some embodiments, the securing mechanism may include an elongated member positionable in an opening extending laterally through the elongated plate and at least one of the bone fasteners. The securing mechanism may include an elongated member positionable in an opening extending laterally through the elongated plate and at least two of the bone fasteners.

In some embodiments, the cervical plate is used in combination with a bone graft. The cervical plate may include a bone graft coupled to the first surface of the elongate plate. The cervical plate may be used in combination with a bone growth promoting material. The bone growth promoting material may include at least one of bone, bone morphogenetic protein, hydroxyapatite, and hydroxyapatite tricalcium phosphate.

In some embodiments, a method may include positioning an elongate plate such that substantially adjacent vertebrae are bridged. The elongate plate may have a first surface and a second surface opposite the first surface. The first surface may be positioned adjacent to at least a portion of a surface of the vertebrae. The elongate plate may include a plurality of openings extending through the elongate plate. The method may include anchoring the plate to the vertebrae. The plate may be anchored to the vertebrae by positioning shafts of a plurality of bone fasteners in at least some of the plurality of openings such that the shaft engages at least one of the vertebrae. The method may include inhibiting a head of at least two of the bone fasteners from being conveyed through the opening such that the bone fasteners couple the elongate plate to the vertebrae. The method may include activating a securing mechanism such that inhibits removal of at least one of the bone fasteners is inhibited. The method may include inhibiting movement of at least the shaft of the bone fastener in a lateral direction using the securing mechanism. The method may include allowing movement of at least the shaft of the bone fastener along a substantially sagittal plane.

BRIEF DESCRIPTION OF THE DRAWINGS

Advantages of the present invention may become apparent to those skilled in the art with the benefit of the following detailed description of the preferred embodiments and upon reference to the accompanying drawings.

Figure 1:
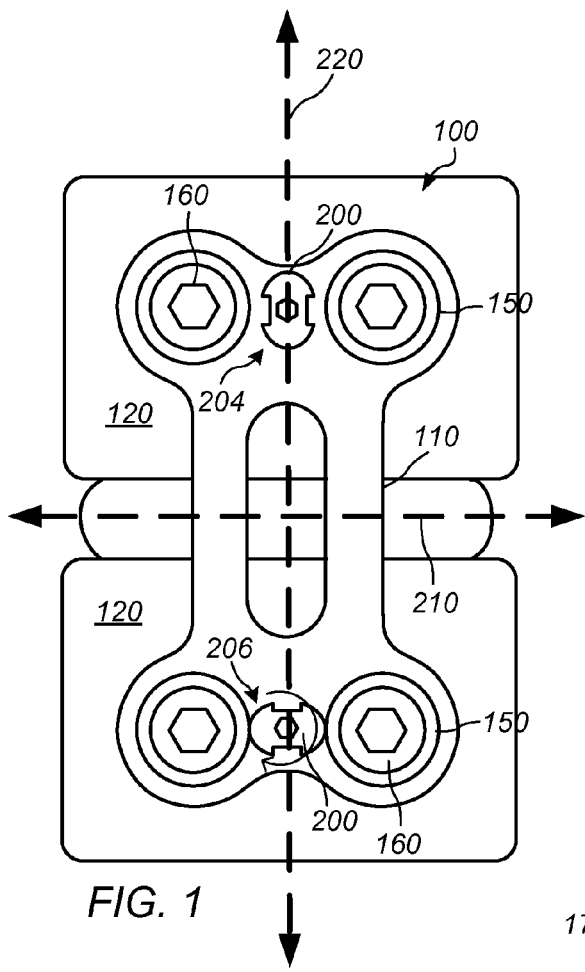
FIG. 1 depicts a diagram of a view of an embodiment of a cervical plate including at least four bone fasteners coupling the plate to two adjacent vertebrae and further including a securing mechanism in an inactivated state and a securing mechanism in an activated state.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

The headings used herein are for organizational purposes only and are not meant to be used to limit the scope of the description. As used throughout this application, the word "may" is used in a permissive sense (i.e., meaning having the potential to), rather than the mandatory sense (i.e., meaning must). The words "include," "including," and "includes" indicate open-ended relationships and therefore mean including, but not limited to. Similarly, the words "have," "having," and "has" also indicated open-ended relationships, and thus mean having, but not limited to. The terms "first," "second," "third," and so forth as used herein are used as labels for nouns that they precede, and do not imply any type of ordering (e.g., spatial, temporal, logical, etc.) unless such an ordering is otherwise explicitly indicated. For example, a "third die electrically connected to the module substrate" does not preclude scenarios in which a "fourth die electrically connected to the module substrate" is connected prior to the third die, unless otherwise specified. Similarly, a "second" feature does not require that a "first" feature be implemented prior to the "second" feature, unless otherwise specified.

Various components may be described as "configured to" perform a task or tasks. In such contexts, "configured to" is a broad recitation generally meaning "having structure that" performs the task or tasks during operation. As such, the component can be configured to perform the task even when the component is not currently performing that task (e.g., a set of electrical conductors may be configured to electrically connect a module to another module, even when the two modules are not connected). In some contexts, "configured to" may be a broad recitation of structure generally meaning "having circuitry that" performs the task or tasks during operation. As such, the component can be configured to perform the task even when the component is not currently on. In general, the circuitry that forms the structure corresponding to "configured to" may include hardware circuits.

Various components may be described as performing a task or tasks, for convenience in the description. Such descriptions should be interpreted as including the phrase "configured to." Reciting a component that is configured to perform one or more tasks is expressly intended not to invoke 35 U.S.C. §112, paragraph six, interpretation for that component.

The scope of the present disclosure includes any feature or combination of features disclosed herein (either explicitly or implicitly), or any generalization thereof, whether or not it mitigates any or all of the problems addressed herein. Accordingly, new claims may be formulated during prosecution of this application (or an application claiming priority thereto) to any such combination of features. In particular, with reference to the appended claims, features from dependent claims may be combined with those of the independent claims and features from respective independent claims may be combined in any appropriate manner and not merely in the specific combinations enumerated in the appended claims.

It is to be understood the present invention is not limited to particular devices or biological systems, which may, of course, vary. It is also to be understood that the terminology used herein is for the purpose of describing particular embodiments only, and is not intended to be limiting. As used in this specification and the appended claims, the singular forms "a", "an", and "the" include singular and plural referents unless the content clearly dictates otherwise. Thus, for example, reference to "a linker" includes one or more linkers.

DETAILED DESCRIPTION

Definitions

Unless defined otherwise, all technical and scientific terms used herein have the same meaning as commonly understood by one of ordinary skill in the art.

The term "connected" as used herein generally refers to pieces which may be joined or linked together.

The term "coupled" as used herein generally refers to pieces which may be used operatively with each other, or joined or linked together, with or without one or more intervening members.

The term "directly" as used herein generally refers to one structure in physical contact with another structure, or, when used in reference to a procedure, means that one process affects another process or structure without the involvement of an intermediate step or component.

The term "sagittal plane" as used herein generally refers to a substantially vertical plane which passes from ventral (front) to dorsal (rear) dividing a body into right and left portions.

This disclosure describes systems and methods including, in some embodiments, a reinforcing plate with a bone fastener securing mechanism centered around the concept of frictional forces in the horizontal direction to prevent back out of fasteners which also semi-constrains the fasteners to allow controlled settling of a graft in the sagittal plane. The securing mechanism may allow settling of the graft such that fastener failure is avoided.

Figure 2:
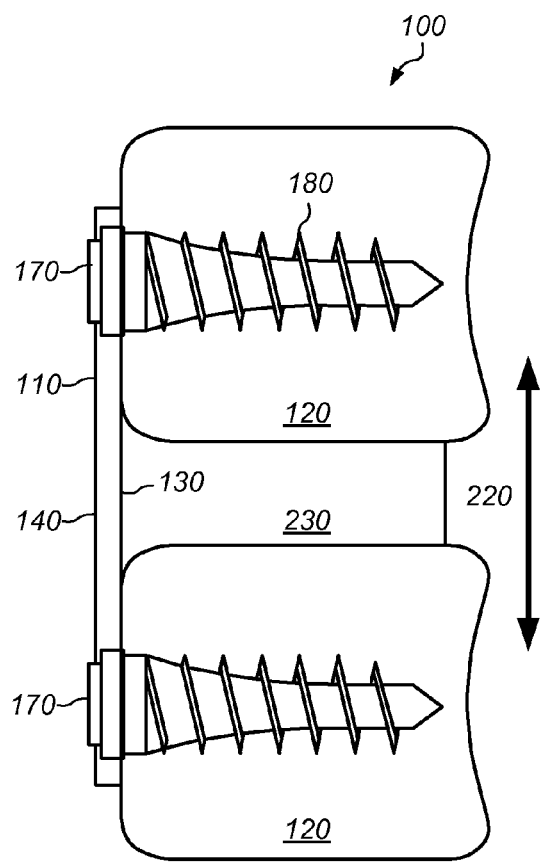
FIG. 2 depicts a diagram of a view of an embodiment of a cervical plate including at least two bone fasteners coupling the plate to two adjacent vertebrae. A graft has been positioned between the two vertebrae.

In some embodiments, reinforcing plate 100 (e.g., a cervical plate) may include elongate plate 110 which bridges, during use, substantially adjacent vertebrae 120 by anchoring the plate to the vertebrae. The elongate plate may have first surface 130 and second surface 140 opposite the first surface. The first surface may be positioned, during use, adjacent to at least a portion of a surface of the vertebrae. The cervical plate may include a plurality of openings 150 extending through the elongate plate. The cervical plate may include a plurality of bone fasteners 160. The bone fasteners may include head 170 and shaft 180. The shaft may be positionable, during use, in the opening such that the shaft engages, during use, at least one of the vertebrae and the head is inhibited from being conveyed through the opening such that the bone fasteners couple the elongate plate to the vertebrae. The cervical plate may include securing mechanism 200. FIG. 1 depicts a diagram of a view of an embodiment of cervical plate 100 including a securing mechanism 200 in an inactivated state 204 and a securing mechanism in an activated state 206. The securing mechanism may, when activated, inhibit removal (e.g., back out) of at least one of the bone fasteners and inhibit movement of at least the shaft of the bone fastener in a lateral direction 210, while allowing movement of at least the shaft of the bone fastener along a substantially sagittal plane 220 (e.g., as depicted in FIGS. 1-2). FIG. 2 depicts a diagram of a view of an embodiment of a cervical plate 100 including at least two bone fasteners 150 coupling the plate to two adjacent vertebrae 120.

Current plates may include securing mechanisms which lock fasteners to the plate such that the fasteners cannot back out or even move at all relative to the plate the fasteners are locked to. This lack of any movement of the fasteners relative to the plate many times results in stresses being applied to the fasteners as the coupled vertebrae settle along the sagittal plane after installation. These stresses have historically resulted in fasteners failing after installation requiring follow up procedures to fix the failed portions and any damage to the subject caused by the failed portions. Securing mechanisms, after activation, described herein are configured to allow limited movement of fasteners in a vertical direction or more accurately along a sagittal plane. Allowing movement of the fasteners in the sagittal plane after installation may relieve fastener stresses due to the movement of the vertebrae (typically due to settling of graft 230 (e.g., as depicted in FIG. 2)) which is installed with a plate during a fusion procedure, and, in addition, increase the probability of boney fusion.

Figure 13A:
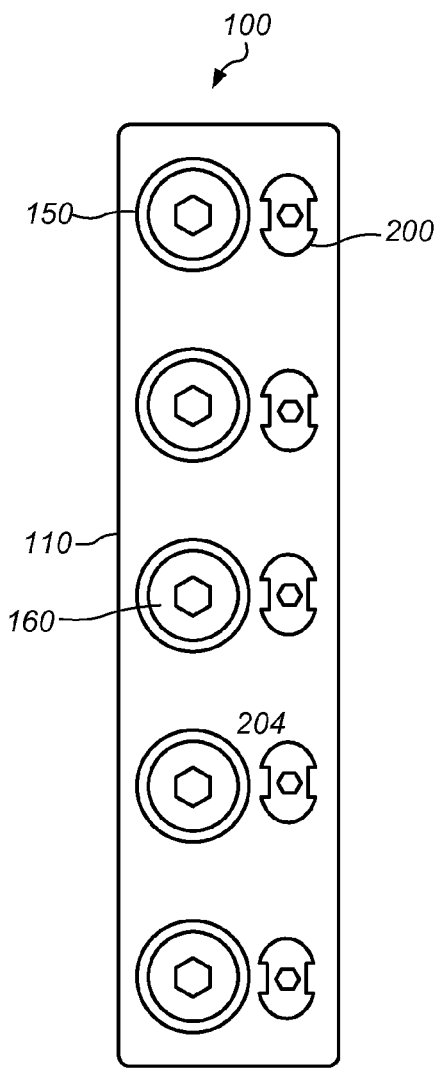
FIGS. 13A-B depict a diagram of a view of an embodiment of a securing mechanism in an inactivated and activated state comprising positionable portions which may be used in combination with a bone reinforcing plate.
Figure 13B:
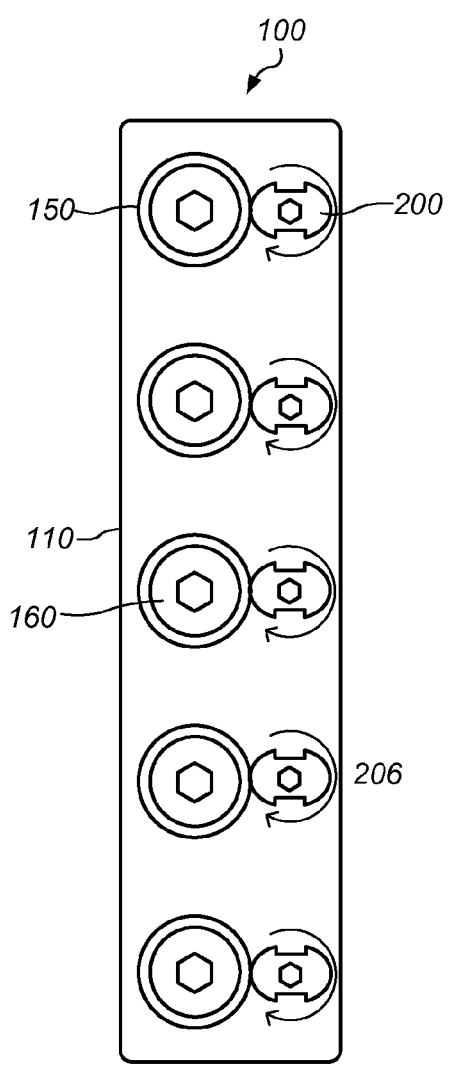

In some embodiments, the securing mechanism, when activated, inhibits backing out of at least one of the bone fasteners from at least one of the plurality of openings. The securing mechanism, when activated, may inhibit removal of at least two of the bone fasteners from at least two of the plurality of openings (e.g., as depicted in FIG. 1). In some embodiments, at least two bone fasteners may be positioned substantially laterally relative to one another (e.g., as depicted in FIG. 1). In some embodiments, at least two bone fasteners are positioned substantially vertically relative to one another (e.g., as depicted in FIGS. 13A-B). In some embodiments, the securing mechanism, when activated, inhibits removal of at least four of the bone fasteners from at least one of the plurality of openings.

In some embodiments, the securing mechanism engages, when activated, a first side of a proximal end (e.g., the head or just below the head along the proximal end of the shaft) of the bone fastener. In some embodiments, the securing mechanism engages, when activated, a first side of head 170 of the bone fastener 160. The securing mechanism may engage, when activated, a first side of the head of the bone fastener such that a second side, opposite of the first side, of the bone fastener engages an adjacent portion of the bone plate forming the opening in which the bone fastener is positioned forming a friction fitting. As depicted in FIG. 1 securing mechanism 200 rotates about an axis from inactivated position 204 to an activated position 206. The ends of the securing mechanism engage heads 170 of such that the heads engage the sides of openings 150 forming a friction fit. The lateral forces applied by the securing mechanism inhibit back out while still allowing movement of the fasteners along the sagittal plane.

Figure 3:
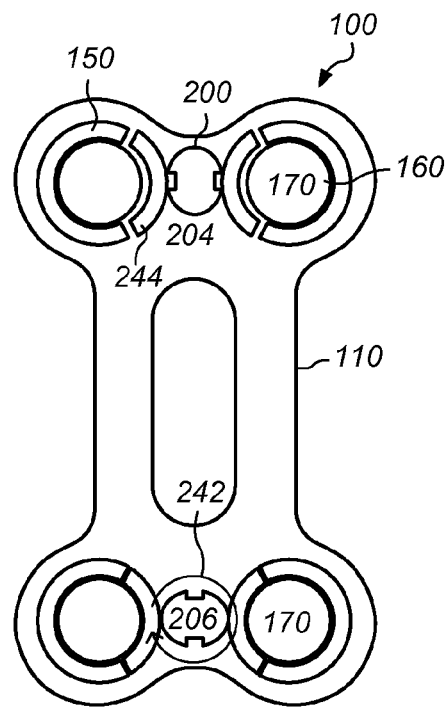
FIG. 3 depicts a diagram of a view of an embodiment of a cervical plate including a securing mechanism in an inactivated state and a securing mechanism in an activated state.

FIG. 3 depicts a diagram of a view of an embodiment of cervical plate 100 including securing mechanism 200 in inactivated state 204 and securing mechanism 200 in activated state 206. As in the embodiment depicted in FIG. 1, securing mechanism 200 rotates 242 about an axis from inactivated position 204 to an activated position 206. The securing mechanism engages, when activated, positionable member 244 which moves from a first unengaged position to a second position engaging a first side of head 170 of the bone fastener forming a friction fitting as the head engages the sides of openings 150.

Figure 4:
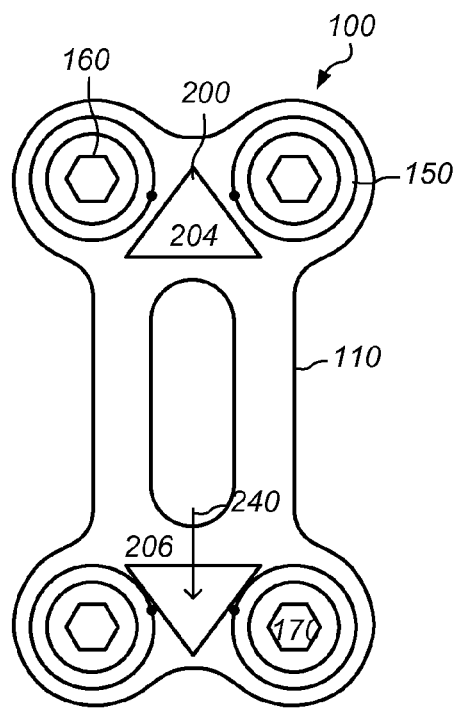
FIG. 4 depicts a diagram of a view of an embodiment of a cervical plate including a securing mechanism in an inactivated state and a securing mechanism in an activated state.

FIG. 4 depicts a diagram of a view of an embodiment of cervical plate 100 including securing mechanism 200 in inactivated state 204 and the securing mechanism in an activated state 206. Securing mechanism 200 may be positionable moving 240 from an inactivated and unengaged state to an activated and engaged state such that substantially lateral forces are applied to the fasteners 160 inhibiting back out.

Figure 5A:
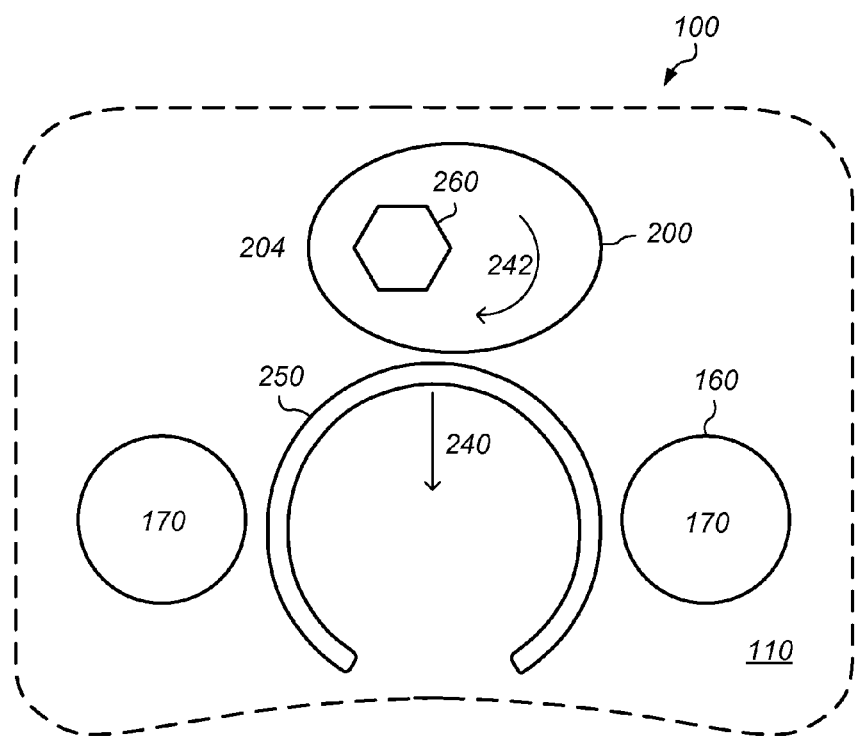
FIGS. 5A-B depict a diagram of a view of an embodiment of a securing mechanism in an inactivated and activated state comprising a screw with a cam-shaped head and a deformable portion which may be used in combination with a cervical plate.
Figure 5B:
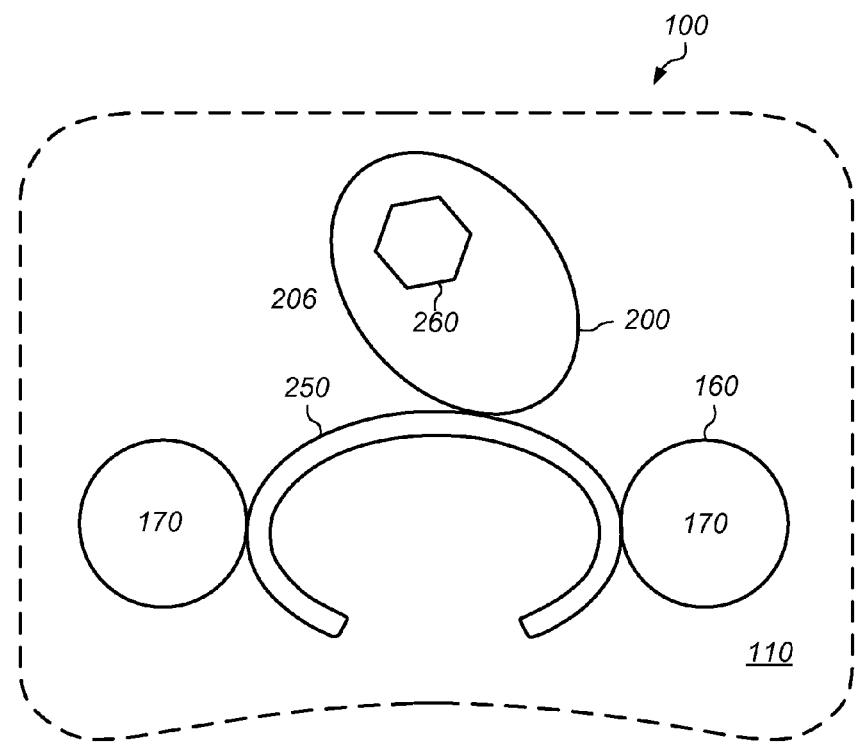

In some embodiments, securing mechanism 200 engages, when activated, deformable portion 250 of cervical plate 100 deforming the deformable portion. FIGS. 5A-B depict a diagram of an view of an embodiment of securing mechanism 200 in inactivated 204 and activated state 206 including screw 260 with a cam-shaped head and deformable portion 260 which may be used in combination with cervical plate 100. In some embodiments, the securing mechanism may include a cam. When the deformable portion deforms, the deformable portion may move from a first unengaged position to a second position. The second position may engage a first side of the head of the bone fastener forming a friction fitting. In the embodiment depicted in FIGS. 5A-B a screw with a cam-shaped head (or in the alternative a simple cam rotationally coupled to the plate surface) rotates such that the extended portion of the cam engages the deformable portion pushing one side in such that the sides press out in reaction. As the sides press out they engage heads 170 of fasteners 160 with a laterally applied force (e.g., as depicted in FIG. 5B).

Figure 6A:
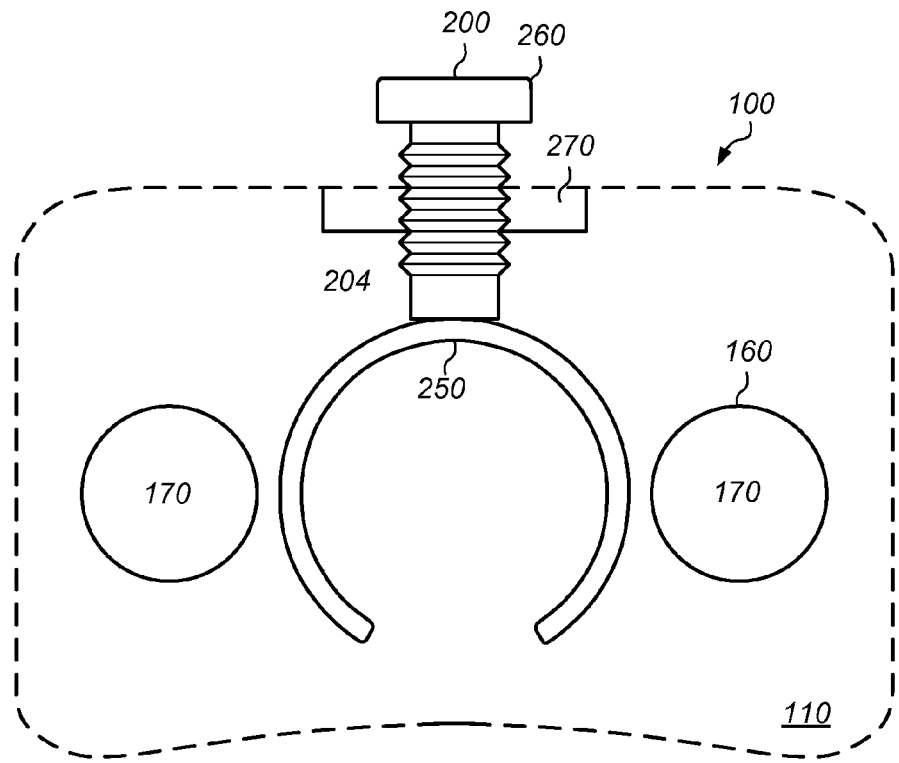
FIGS. 6A-B depict a diagram of a view of an embodiment of a securing mechanism in an inactivated and activated state comprising a screw and a deformable portion which may be used in combination with a cervical plate.
Figure 6B:
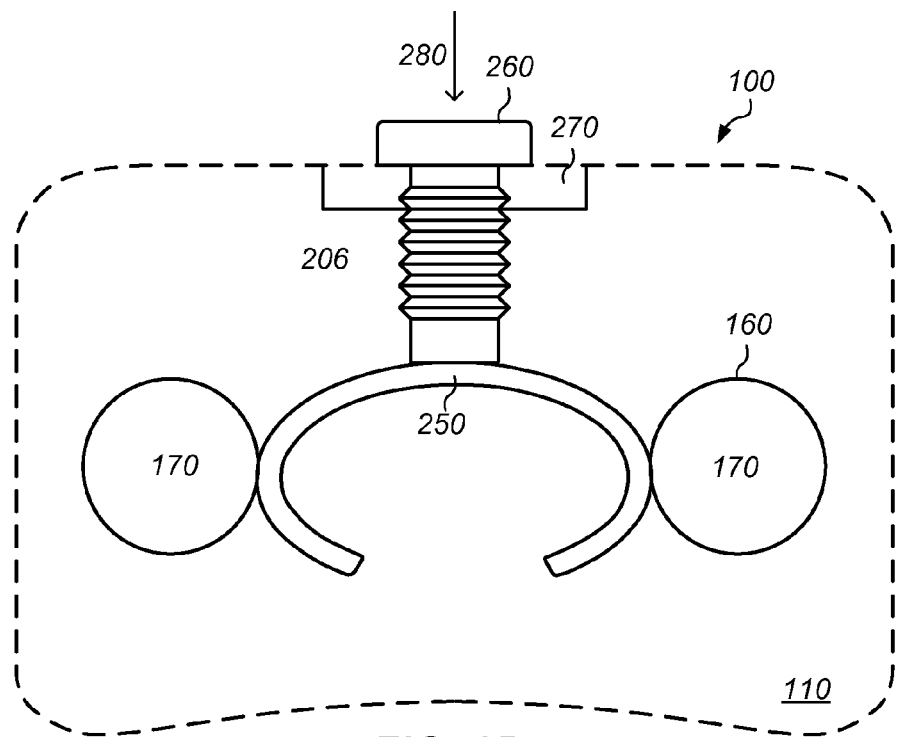

In some embodiments, securing mechanism 200 comprises screw 260 which is conveyed, when the securing mechanism is activated, into opening 270 adjacent deformable portion 250 such that the conveyance 280 of the screw into the opening deforms the deformable portion. FIGS. 6A-B depict a diagram of a view of an embodiment of securing mechanism 200 in inactivated 204 and activated 206 state comprising screw 260 and deformable portion 250 which may be used in combination with cervical plate 100. When the deformable portion deforms, the deformable portion may move from a first unengaged position to a second position. The second position may engage a first side of the head of the bone fastener such that an opposing side of the head of the bone fastener engages a side of the opening in which the fastener is positioned forming a friction fitting.

Figure 7A:
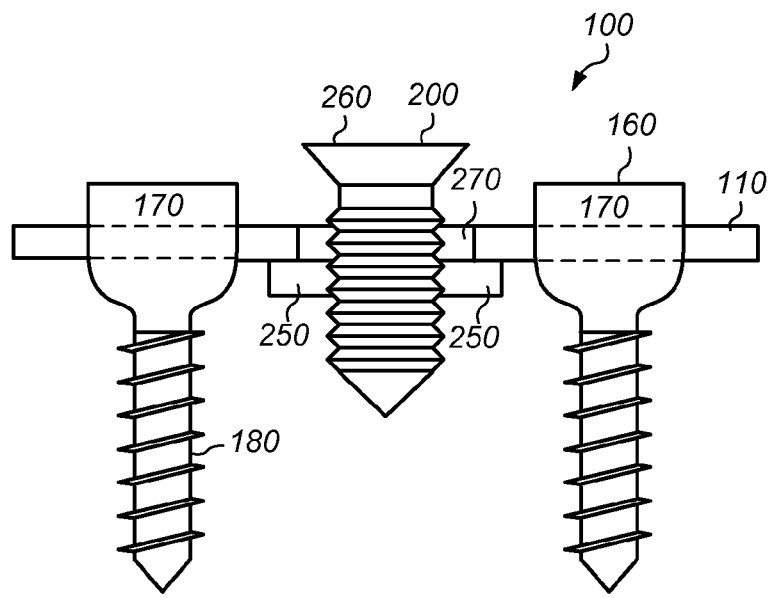
FIGS. 7A-B depict a diagram of an cross-sectional view of an embodiment of a securing mechanism in an inactivated and activated state comprising a screw and a deformable portion which may be used in combination with a cervical plate.
Figure 7B:
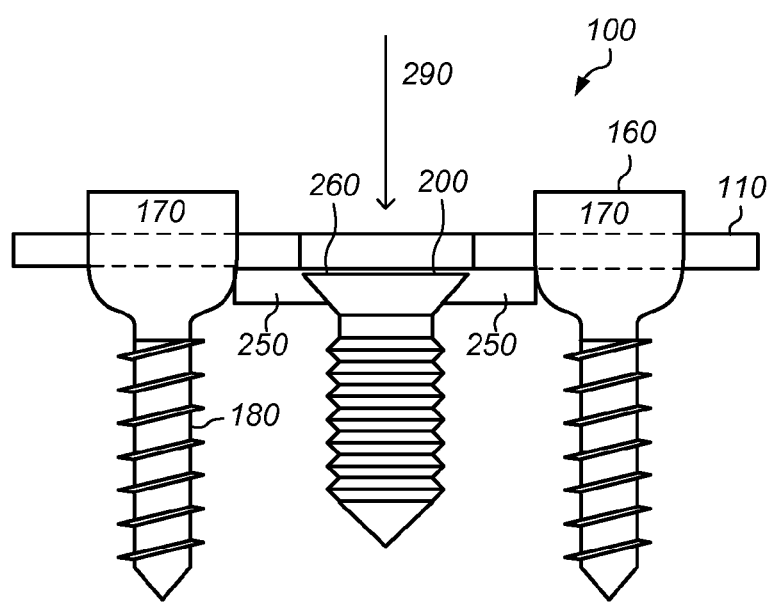

In some embodiments, the securing mechanism engages, when activated, a deformable portion of the cervical plate deforming the deformable portion. FIGS. 7A-B depict a diagram of a cross-sectional view of an embodiment of securing mechanism 200 in inactivated 204 and activated 206 state comprising screw 260 and deformable portions 250 which may be used in combination with cervical plate 100. In the current embodiment a head of screw 260 may be conveyed 290 into opening 270 deforming deformable portion 250 when engaged by the head displacing the deformable portion such that the deformable portion engages with a lateral force fasteners 160. In some embodiments, the deformable portion may include a ring which expands upon activation of the securing mechanism.

Figure 8A:
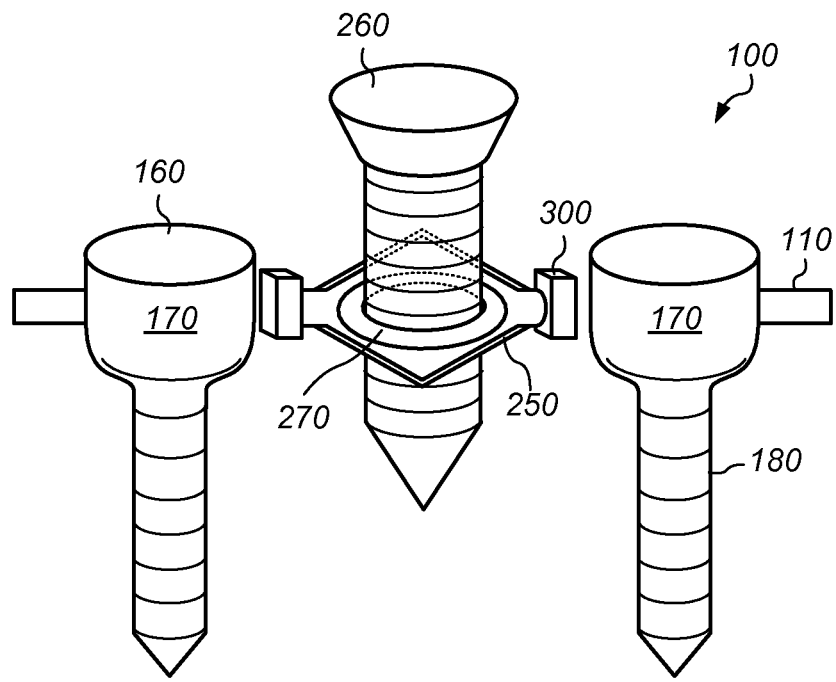
FIGS. 8A-B depict a diagram of a cross-sectional view of an embodiment of a securing mechanism in an inactivated and activated state comprising a screw and a deformable portion which may be used in combination with a cervical plate.
Figure 8B:
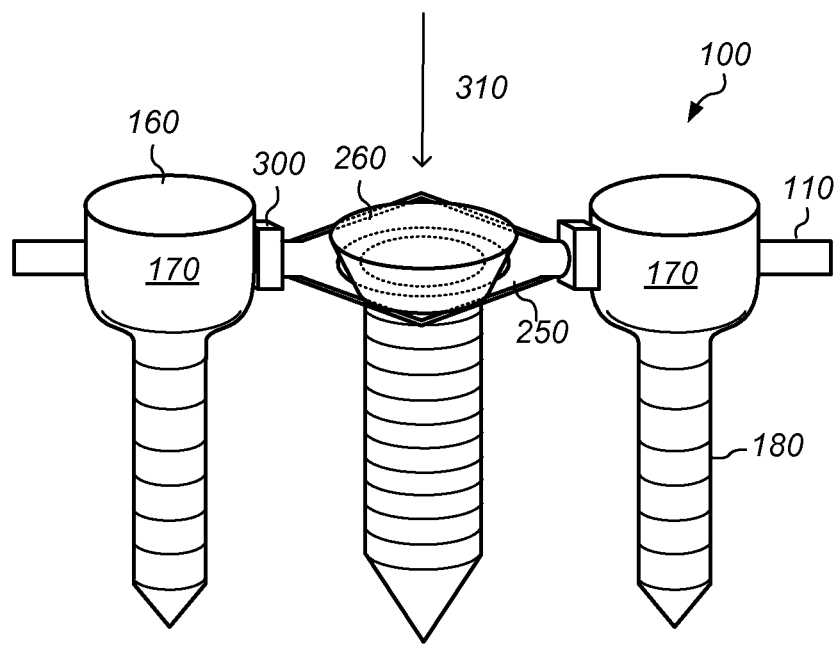

In some embodiments, a deformable portion may function to reposition an engaging portion of a securing mechanism when activated to exert lateral forces on fasteners of a plate. FIGS. 8A-B depict a diagram of a cross-sectional view of an embodiment of securing mechanism 200 in inactivated 204 and activated 206 state comprising screw 260, deformable portion 250, and engaging portion 300 which may be used in combination with cervical plate 100. The screw may be conveyed 310, when the securing mechanism is activated, into opening 270 such that a head of the screw engages a first side of head 170 of bone fastener 160. The deformable portion deforms such that an engaging portion coupled to the deformable portion moves from a first unengaged position to a second position engaging a first side of the head of the bone fastener applying a lateral force forming a friction fitting between the engaging portion, the head and an opening in the plate wherein the fastener is positioned. The deformable portion deforms in response to the head of the screw pushing against the deformable portion extending out opposing corners of the deformable portion.

Figure 9A:
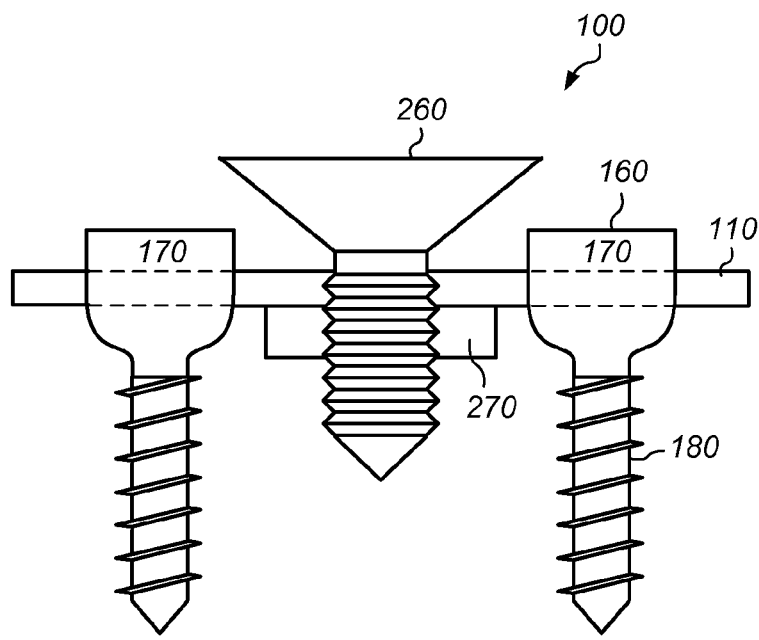
FIGS. 9A-B depict a diagram of a view of an embodiment of a securing mechanism in an inactivated and activated state comprising a screw which may be used in combination with a cervical plate.
Figure 9B:
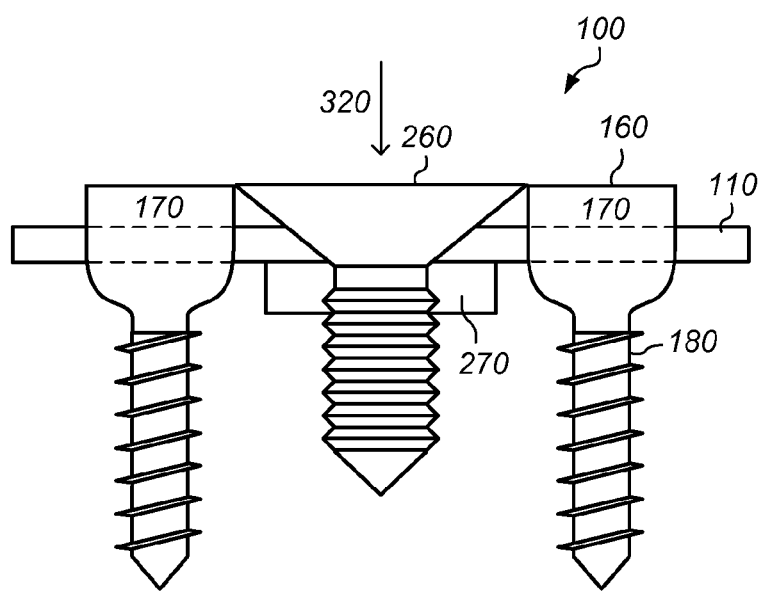

In some embodiments, the securing mechanism may include a screw. FIGS. 9A-B depict a diagram of a view of an embodiment of securing mechanism 200 in inactivated 204 and activated 206 state comprising screw 260 which may be used in combination with cervical plate 100. The screw may be conveyed 320, when the securing mechanism is activated, into opening 270 such that a head of the screw engages a first side of heads 170 of bone fasteners 160. The screw may engage the first side of the bone fastener such that a second side, opposite of the first side, of the bone fastener engages an adjacent portion of the cervical plate forming the opening in which the bone fastener is positioned forming a friction fitting. The head of screw 260 may apply lateral forces to heads 170 of fasteners 160 such that a friction fit is formed between the head of screw 260, heads 170 and portions of plate 110 forming the openings on opposing sides to screw 260.

Figure 10A:
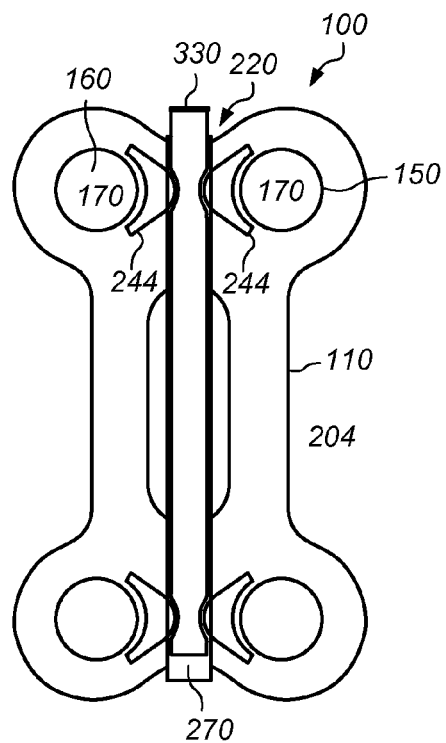
FIGS. 10A-B depict a diagram of a view of an embodiment of a securing mechanism in an inactivated and activated state comprising an elongated member and positionable portions which may be used in combination with a cervical plate.
Figure 10B:
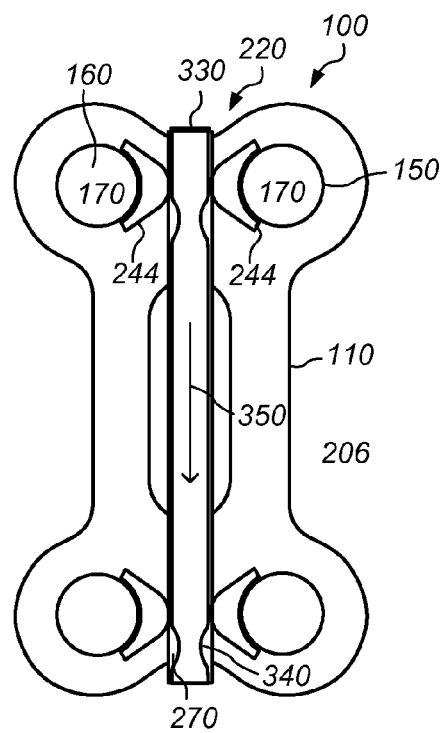

In some embodiments, the securing mechanism may include a positionable member for each fastener and an elongated member positionable in an opening through the elongated plate. FIGS. 10A-B depict a diagram of a view of an embodiment of securing mechanism 200 in inactivated 204 and activated 206 state comprising elongated member 330 and positionable members 244 which may be used in combination with cervical plate 100. The securing mechanism may include an elongated member positionable in opening 270 extending along a longitudinal axis through the elongated plate. The elongated member may be positionable in the longitudinal opening in the plate. Indentations 340 along the elongated member may have a smaller diameter than the remaining portions of the elongated member. In inactivated state 204 the positionable members may be situated at a first position such that a portion of the positionable members sit within indentations 340 adjacent to the elongated member. The securing mechanism may be activated by repositioning 350 elongated member 330 from a first position (depicted in FIG. 10A) to a second position (depicted in FIG. 10B). Repositioning the elongated member may convey positionable members from the first position (depicted in FIG. 10A) to a second position (depicted in FIG. 10B) due to the increasing diameter of the elongated member applying a lateral force to the positionable members which in turn convey that lateral force to head 170 of fasteners 160 pressing the head against the plate.

Figure 11A:
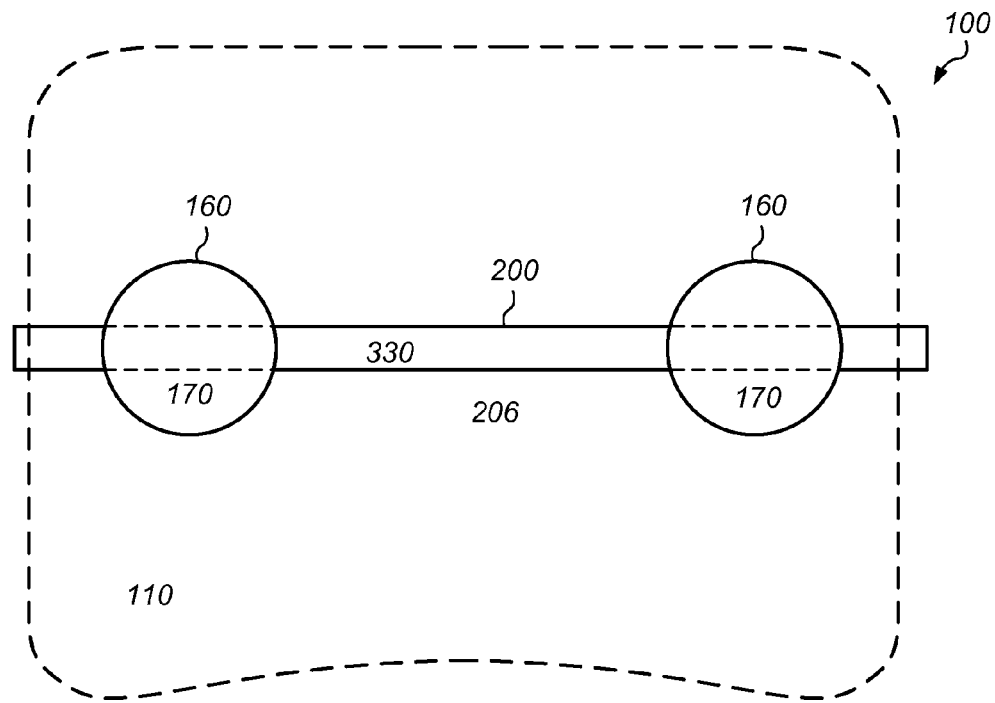
FIGS. 11A-B depict a diagram of an overhead and a side view of an embodiment of the heads of two bone fasteners and a securing mechanism comprising an elongated member in an activated state.
Figure 11B:
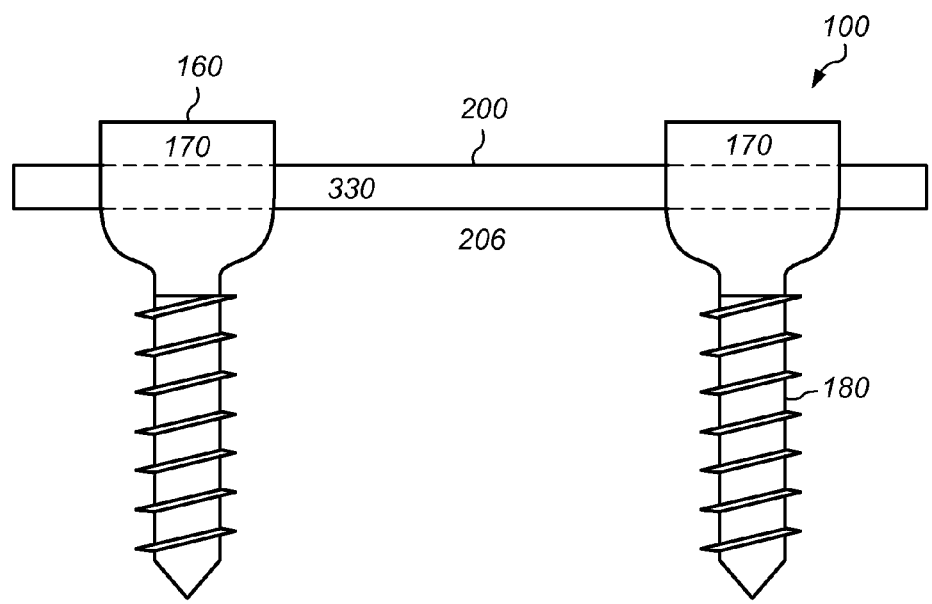

In some embodiments, the securing mechanism may include an elongated member positionable in an opening extending laterally through the elongated plate and at least one of the bone fasteners. FIGS. 11A-B depict a diagram of an overhead and a side view of an embodiment of heads 170 of two bone fasteners 160 and securing mechanism 200 comprising elongated member 330 in activated state 206. The elongated member may extend through an opening extending through the plate and abutting at least one head of a fastener inhibiting back out while allowing some movement along the sagittal plane relieving stress on the fasteners. The opening may include one or more stops which inhibit the elongated member from moving beyond a certain point. The elongated member may be positioned through only one side of the plate due to the one or more stops. In some embodiments, a plate may include an elongated member for each fastener providing advantages such as requiring less available space to insert the elongate member (due to the fact the elongated member is shorter since it does not have to extend through the entire width of the plate) during use.

Figure 12A:
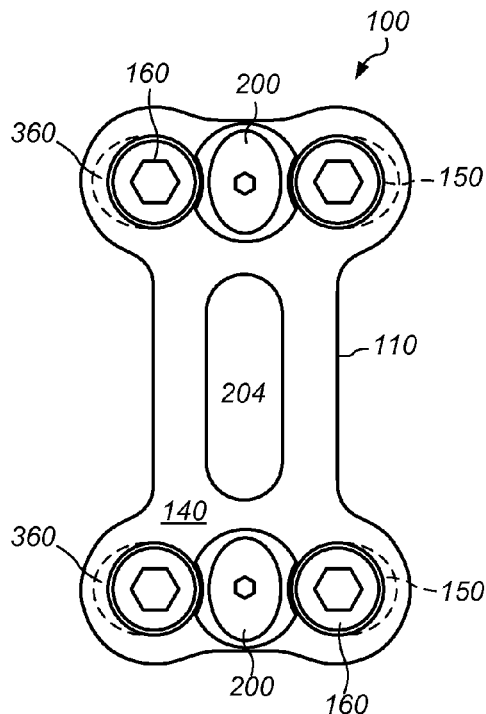
FIGS. 12A-B depict a diagram of a view of an embodiment of a securing mechanism in an inactivated and activated state which may be used in combination with a bone reinforcing plate.
Figure 12B:
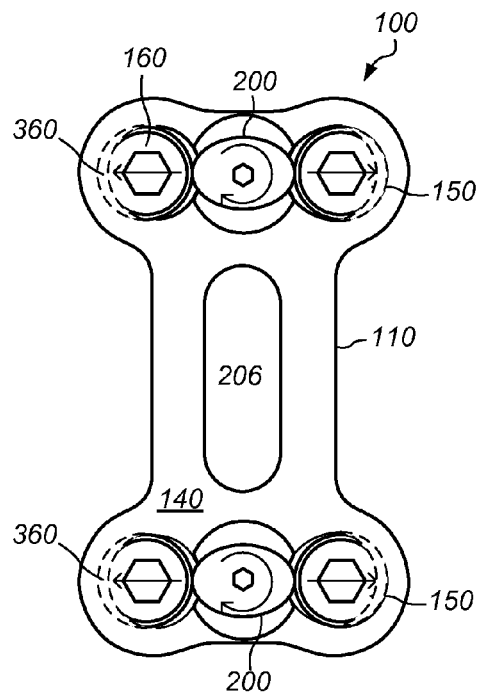

FIGS. 12A-B depict a diagram of a view of an embodiment of securing mechanism 200 in an inactivated and activated state which may be used in combination with a reinforcing plate 100. Securing mechanism 200 may include a cam (e.g., as depicted in FIGS. 12A-B). The cam may rotate from an inactivated 204 to an activate 206 state. Fasteners 160 may be positionable in openings 150. The opening may extend within the plate such that lip 360 (formed in surface 140) extends over a portion of the opening. As the cam is rotated from an inactivated state to an activated state the cam applies a lateral force against heads 170 of fasteners 160 such that at least a portion of the opposing side of the heads are positioned beneath lip 360 inhibiting back out and allowing controlled movement of the fasteners along certain predetermined planes.

In some embodiments, the cervical plate is used in combination with a graft (e.g., as depicted by bone graft 230 in FIG. 2). The cervical plate may include a bone graft coupled to the first surface of the elongate plate. The cervical plate may be used in combination with a bone growth promoting material. The bone growth promoting material may include at least one of bone, bone morphogenetic protein, hydroxyapatite, and hydroxyapatite tricalcium phosphate. Bone growth promoting materials may include, but are not limited to, bone, bone morphogenetic proteins, hydroxyapatite, genes coding for the production of bone, or any other material that intrinsically participates in the growth of bone from one of the adjacent vertebral bodies to the other of the adjacent vertebral bodies at the fusion site. Plate systems herein may be combined with a chemical substance to inhibit scar formation.

Although herein plates have been described as being typically used for cervical reinforcement and fusion procedures, the plates and securing mechanisms may be used for other purposes with little adaptation. FIGS. 13A-B depict a diagram of a view of an embodiment of securing mechanism 200 in inactivated 204 and activated 206 state comprising positionable portions which may be used in combination with a reinforcing plate 100. The plate depicted in FIGS. 13A-B may be used to reinforce other bones in the body, elongated bones for example which may be found in the arms or legs. Other shapes as needed may be used for other bone reinforcing/fusing purposes. The securing mechanism depicted in FIGS. 13A-B functions in a similar manner as the securing mechanism depicted in FIG. 1.

In some embodiments, a method may include positioning an elongate plate such that substantially adjacent vertebrae are bridged. The elongate plate may have a first surface and a second surface opposite the first surface. The first surface may be positioned adjacent to at least a portion of a surface of the vertebrae. The elongate plate may include a plurality of openings extending through the elongate plate. The method may include anchoring the plate to the vertebrae. The plate may be anchored to the vertebrae by positioning shafts of a plurality of bone fasteners in at least some of the plurality of openings such that the shaft engages at least one of the vertebrae. The method may include inhibiting a head of at least two of the bone fasteners from being conveyed through the opening such that the bone fasteners couple the elongate plate to the vertebrae. The method may include activating a securing mechanism such that inhibits removal of at least one of the bone fasteners is inhibited. The method may include inhibiting movement of at least the shaft of the bone fastener in a lateral direction using the securing mechanism. The method may include allowing movement of at least the shaft of the bone fastener along a substantially sagittal plane.

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A cervical plate, comprising:
an elongate plate which bridges, during use, substantially adjacent vertebrae by anchoring the plate to the vertebrae, the elongate plate having a first surface and a second surface opposite the first surface, wherein the first surface is positioned, during use, adjacent to at least a portion of a surface of the vertebrae;
a plurality of openings extending through the elongate plate;
a plurality of bone fasteners comprising a head and a shaft, wherein the shaft is positionable, during use, in the opening such that the shaft engages, during use, at least one of the vertebrae and the head is inhibited from being conveyed through the opening such that the bone fasteners couple the elongate plate to the vertebrae; and
a securing mechanism directly connected to the elongate plate which when activated inhibits removal of at least two of the bone fasteners from the openings and inhibits movement of at least the shafts of the bone fasteners in a lateral direction, while allowing movement of at least the shafts of the bone fasteners substantially parallel to a sagittal plane, wherein when the securing mechanism is activated the heads of the bone fasteners are inhibited from translational movement relative to the elongate plate substantially parallel to a sagittal plane.

2. The cervical plate of claim 1, wherein the securing mechanism, when activated, inhibits backing out of at least one of the bone fasteners from at least one of the plurality of openings.

3. The cervical plate of claim 1, wherein the securing mechanism, when activated, inhibits removal of at least two of the bone fasteners from at least one of the plurality of openings, and wherein the at least two bone fasteners are positioned substantially laterally relative to one another.

4. The cervical plate of claim 1, wherein the securing mechanism, when activated, inhibits removal of at least two of the bone fasteners from at least one of the plurality of openings, and wherein the at least two bone fasteners are positioned substantially vertically relative to one another.

5. The cervical plate of claim 1, wherein the securing mechanism, when activated, inhibits removal of at least four of the bone fasteners from at least one of the plurality of openings.

6. The cervical plate of claim 1, wherein the securing mechanism engages, when activated, a first side of the head of the bone fastener.

7. The cervical plate of claim 1, wherein the securing mechanism engages, when activated, a first side of the head of the bone fastener such that a second side, opposite of the first side, of the bone fastener engages an adjacent portion of the cervical plate forming the opening in which the bone fastener is positioned forming a friction fitting.

8. The cervical plate of claim 1, wherein the securing mechanism comprises a cam.

9. The cervical plate of claim 1, wherein the securing mechanism engages, when activated, a positionable member which moves from a first unengaged position to a second position engaging a first side of the head of the bone fastener forming a friction fitting.

10. The cervical plate of claim 1, wherein the securing mechanism engages, when activated, a deformable portion of the cervical plate deforming the deformable portion which moves from a first unengaged position to a second position engaging a first side of the head of the bone fastener forming a friction fitting.

11. The cervical plate of claim 10, wherein the deformable portion comprises a ring which expands upon activation of the securing mechanism.

12. The cervical plate of claim 10, wherein the securing mechanism comprises a screw which is conveyed, when the securing mechanism is activated, into an opening adjacent the deformable portion such that the conveyance of the screw into the opening deforms the deformable portion.

13. The cervical plate of claim 1, wherein the securing mechanism comprises a screw which is conveyed, when the securing mechanism is activated, into an opening such that a head of the screw engages a first side of the head of the bone fastener such that a second side, opposite of the first side, of the bone fastener engages an adjacent portion of the cervical plate forming the opening in which the bone fastener is positioned forming a friction fitting.

14. The cervical plate of claim 1, wherein the securing mechanism engages, when activated, a deformable portion of the cervical plate deforming the deformable portion which moves an engaging portion coupled to the deformable portion from a first unengaged position to a second position engaging a first side of the head of the bone fastener forming a friction fitting.

15. The cervical plate of claim 1, wherein the securing mechanism comprises an elongated member positionable in an opening extending laterally through the elongated plate and at least one of the bone fasteners.

16. The cervical plate of claim 1, wherein the securing mechanism comprises an elongated member positionable in an opening extending laterally through the elongated plate and at least two of the bone fasteners.

17. A bone plate, comprising:
an elongate plate which bridges, during use, substantially adjacent bone portions by anchoring the plate to the bone portions, the elongate plate having a first surface and a second surface opposite the first surface, wherein the first surface is positioned, during use, adjacent to at least a portion of a surface of the bone portions;
a plurality of openings extending through the elongate plate;

a plurality of bone fasteners comprising a head and a shaft, wherein the shaft is positionable, during use, in the opening such that the shaft engages, during use, at least one of the bone portions and the head is inhibited from being conveyed through the opening such that the bone fasteners couple the elongate plate to the bone portions; and a securing mechanism directly connected to the elongate plate which when activated inhibits removal of at least two of the bone fasteners from the openings and inhibits movement of at least the shafts of the bone fasteners in a first direction, while allowing movement of at least the shafts of the bone fasteners in a second direction substantially orthogonal to the first direction, wherein when the securing mechanism is activated the heads of the bone fasteners are inhibited from translational movement relative to the elongate plate.

18. The bone plate of claim 17, wherein the securing mechanism, when activated, inhibits backing out of at least one of the bone fasteners from at least one of the plurality of openings.

19. The bone plate of claim 17, wherein the securing mechanism engages, when activated, a first side of the head of the bone fastener.

20. The bone plate of claim 17, wherein the securing mechanism engages, when activated, a first side of the head of the bone fastener such that a second side, opposite of the first side, of the bone fastener engages an adjacent portion of the bone plate forming the opening in which the bone fastener is positioned forming a friction fitting.

21. The bone plate of claim 17, wherein the securing mechanism engages, when activated, a positionable member which moves from a first unengaged position to a second position engaging a first side of the head of the bone fastener forming a friction fitting.

22. The bone plate of claim 17, wherein the securing mechanism engages, when activated, a deformable portion of the cervical plate deforming the deformable portion which moves from a first unengaged position to a second position engaging a first side of the head of the bone fastener forming a friction fitting.

23. A method, comprising:
positioning an elongate plate such that substantially adjacent vertebrae are bridged, the elongate plate having a first surface and a second surface opposite the first surface, wherein the first surface is positioned adjacent to at least a portion of a surface of the vertebrae, and wherein the elongate plate comprises a plurality of openings extending through the elongate plate;
anchoring the plate to the vertebrae by positioning shafts of a plurality of bone fasteners in at least some of the plurality of openings such that the shaft engages at least one of the vertebrae;
inhibiting a head of at least two of the bone fasteners from being conveyed through the opening such that the bone fasteners couple the elongate plate to the vertebrae;
activating a securing mechanism directly connected to the elongate plate such that removal of at least one of the bone fasteners is inhibited;
engaging a first side of the head of the bone fastener, using the securing mechanism, such that a second side, opposite of the first side, of the bone fastener engages an adjacent portion of the elongate plate forming the opening in which the bone fastener is positioned forming a friction fitting;
inhibiting movement of at least the shaft of the bone fastener in a lateral direction using the securing mechanism;
inhibiting translational movement of the head of the bone fastener relative to the elongate plate and substantially parallel to a sagittal plane using the securing mechanism; and
allowing movement of at least the shaft of the bone fastener substantially parallel to a sagittal plane.

24. The method of claim 23, further comprising activating the securing mechanism such that backing out of at least one of the bone fasteners from at least one of the plurality of openings is inhibited.

25. The method of claim 23, further comprising engaging a positionable member, using the securing mechanism, such that the positionable member moves from a first unengaged position to a second position engaging a first side of the head of the bone fastener forming a friction fitting.

26. The method of claim 23, further comprising engaging a deformable portion of the cervical plate, using the securing mechanism, deforming the deformable portion which moves from a first unengaged position to a second position engaging a first side of the head of the bone fastener forming a friction fitting.

27. A method, comprising:
positioning an elongate plate such that substantially adjacent bone portions are bridged, the elongate plate having a first surface and a second surface opposite the first surface, wherein the first surface is positioned adjacent to at least a portion of a surface of the bone portions, and wherein the elongate plate comprises a plurality of openings extending through the elongate plate;
anchoring the plate to the bone portions by positioning shafts of a plurality of bone fasteners in at least some of the plurality of openings such that the shaft engages at least one of the bone portions;
inhibiting a head of at least two of the bone fasteners from being conveyed through the opening such that the bone fasteners couple the elongate plate to the bone portions;
activating a securing mechanism directly connected to the elongate plate such that removal of at least one of the bone fasteners is inhibited;
engaging a first side of the head of the bone fastener, using the securing mechanism, such that a second side, opposite of the first side, of the bone fastener engages an adjacent portion of the elongate plate forming the opening in which the bone fastener is positioned forming a friction fitting;
inhibiting movement of at least the shaft of the bone fastener in a first direction using the securing mechanism;
allowing movement of at least the shaft of the bone fastener in a second direction substantially orthogonal to the first direction; and
inhibiting translational movement of at least the head of the bone fastener relative to the elongate plate in the second direction using the securing mechanism.

28. The method of claim 27, further comprising activating the securing mechanism such that backing out of at least one of the bone fasteners from at least one of the plurality of openings is inhibited.

29. The method of claim 27, further comprising engaging a positionable member, using the securing mechanism, such that the positionable member moves from a first unengaged position to a second position engaging a first side of the head of the bone fastener forming a friction fitting.

30. The method of claim 27, further comprising engaging a deformable portion of the cervical plate, using the securing mechanism, deforming the deformable portion which moves from a first unengaged position to a second position engaging a first side of the head of the bone fastener forming a friction fitting.

* * * * *